United States Patent [19]

Bätz et al.

[11] 4,386,212

[45] May 31, 1983

[54] PROCESS FOR THE PRODUCTION OF 5-(4'-CHLORO-5'-SULFAMOYL-2'-THENYLAMINO)-PHENYLTETRAZOLE

[75] Inventors: Friedrich Bätz, Einhausen; Karl Lauer, Schriesheim, both of Fed. Rep. of Germany

[73] Assignee: Boehringer Manheim GmbH, Mannheim, Fed. Rep. of Germany

[21] Appl. No.: 289,934

[22] Filed: Aug. 4, 1981

[30] Foreign Application Priority Data

Sep. 13, 1980 [DE] Fed. Rep. of Germany ....... 3034664

[51] Int. Cl.³ ............................................. C07D 257/04
[52] U.S. Cl. ..................................... 548/252; 542/423
[58] Field of Search ......................... 548/252; 542/423

[56] References Cited

U.S. PATENT DOCUMENTS 3,665,002  5/1972  Popelak ................................ 548/252

OTHER PUBLICATIONS

Cram et al., Org. Chem., p. 379, McGraw Hill, N.Y., N.Y., (1964).
Organic Syn., vol. I, p. 80.

Primary Examiner—Donald G. Daus
Assistant Examiner—D. Springer
Attorney, Agent, or Firm—Felfe & Lynch

[57] ABSTRACT

The present invention provides a process for the preparation of 5-(4'-chloro-5'-sulfamoyl-2'-thenylamino)-phenyltetrazole by condensing 5-(4'-chloro-5'-sulfamoyl-2'-aminophenyl)-tetrazole with thiophene-2-aldehyde in the presence of an acid catalyst and reducing the 5-[4'-chloro-5'-sulfamoyl-2'-(thenylidene-2-amino)-phenyl]tetrazole so obtained with a boranate, wherein the condensation is carried out in dimethyl sulfoxide as solvent, with azeotropic distilling off of the water formed and the reduction is carried out in the same medium, without isolation of the 5-[4'-chloro-5'-sulfamoyl-2'-(thenylidene-2-amino)-phenyl]-tetrazole.

10 Claims, No Drawings

PROCESS FOR THE PRODUCTION OF 5-(4'-CHLORO-5'-SULFAMOYL-2'-THENYLAMINO)-PHENYLTETRAZOLE

This invention relates to a new and improved process for the preparation of 5-(4'-chloro-5'-sulfamoyl-2'-thenylamino)-phenyltetrazole.

5-(4'-Chloro-5'-sulfamoyl-2'-thenylamino)-phenyltetrazole (INN azosemide) possesses valuable diuretic and saluretic activities. The compound and several processes for the preparation thereof are described, for example, in U.S. Pat. No. 3,665,002. Because of the complex structure of this compound, the synthesis must, in every case, take place via a series of individual steps, which proceed with more or less good yields so that, according to the teachings of the above-mentioned U.S. patent, it is only possible to achieve an extremely low overall yield.

Consequently, there is a need for a new synthesis which gives high yields and which, if possible, makes use of economic starting materials and can be carried out on a large scale in as simple a manner as possible, without giving rise to environmental problems.

Surprisingly, this problem can be solved by an alteration of the process described in Example 2 of the above-mentioned U.S. patent for the preparation of a another compound which, according to the teachings of this patent, takes place with an extremely poor yield of only 22% in the last step.

Thus, according to the present invention, there is provided a process for the preparation of 5-(4'-chloro-5'-sulfamoyl-2'-thenylamino)-phenyltetrazole by condensing 5-(4'-chloro-5'-sulfamoyl-2'-aminophenyl)-tetrazole with thiophene-2-aldehyde in the presence of an acid catalyst and reducing the 5-[4'-chloro-5'-sulfamoyl-2'-(thenyliden-2-amino)-phenyl]-tetrazole so obtained with a boranate, wherein the condensation is carried out in dimethyl sulphoxide as solvent, with azeotropic distilling off of the water formed and the reduction of the 5-[4'-chloro-5'-sulfamoyl-2'-(thenyliden-2-amino)-phenyl]-tetrazole is carried out in the same medium, without isolation.

The 5-(4'-chloro-5'-sulfamoyl-2'-aminophenyl)-tetrazole (amine III) used as starting material is obtained analogously to the process described in U.S. Pat. No. 3,665,002 by the sulphochlorination of 5-(4'-chloro-2'-aminophenyl)-tetrazole and subsequent reaction with ammonia.

Extensive experiments have shown that the reaction of Amine III with thiophene-2-aldehyde to give the Schiff base, i.e. 5-[4'-chloro-5'-sulfamoyl-2'-(thenyliden-2-amino)-phenyl]-tetrazole, only proceeds with the high yields obtained by the process according to the present invention when, instead of the usual solvents, dimethyl sulphoxide (DMSO) is used as solvent and the water formed by the reaction is continuously removed from the system by azeotropic distillation. Removal of the water by means of water-binding agents, such as phosphorus pentoxide or anhydrous sodium sulphate, as is suggested, for example, in U.S. Pat. No. 3,665,002, does not give the same result. Since, when carrying out this distillation, a part of the thiophenealdehyde also distils over, it has proved to be necessary to use this in excess, 1.1 to 3 mole of aldehyde and preferably 1.5 to 2 mole of aldehyde being used per mole of amine. A larger excess of thiophenealdehyde is not necessary and also has no point since any excess remaining in the reaction solution unnecessarily uses up reducing agent in the subsequent reduction and the end product is thereby contaminated.

The reaction is normally carried out at a temperature of from 20° to 100° C., a temperature of 40° to 100° C. being preferred and a temperature of 45° to 70° C. being especially preferred. The azeotropic distilling off of the solvent is achieved by the application of a low vacuum, the addition of water-entraining agents, such as benzene, toluene or similar solvents forming low boiling point azeotropes with water thereby proving to be useful. Depending upon the reaction temperature and the concentrations of the reaction components employed, reaction times of about 0.5 to 24 hours and especially of 1 to 3 hours have proved to be sufficient.

The formation of the Schiff base is promoted in known manner by the addition of a small amount of an acid catalyst. Catalysts which have proved to be especially useful include mineral acids, such as phosphoric acid, polyphosphoric acid, sulphuric acid, hydrochloric acid and the like, as well as Lewis acids, such as zinc chloride and aluminium chloride. About 0.05 to 0.5 mole equivalents of catalyst are preferably used, referred to the amount of amine employed.

In contradistinction to the method described in U.S. Pat. No. 3,665,002, the reduction of the Schiff base is not carried out after isolation of the compound and introduction into an aqueous methanolic solution which is per se preferred for the reaction with sodium boronate but rather directly in the reaction medium, i.e., in dimethyl sulphoxide or dimethylformamide as a solvent. This is possible since, due to the manner in which the previous stage is carried out, the Schiff base is formed in almost quantitative yield so that, in the subsequent reduction, the desired azosemide is obtained in very pure form, and, in particular, a resplitting of the Schiff base to give te amine is prevented due to the anhydrous medium used.

Apart from the sodium boronate usually employed for reducing the Schiff base, there can, in particular, also be used potassium boranate since this contributes towards an even more homogeneous reaction and thus to increased yields. It has proved to be desirable to add about 2 to 10 and preferably 2 to 4 mole equivalents of boronate since, besides the reduction of the Schiff base, the excess of thiophenealdehyde must also be reduced and a partial decomposition of the hydride by other side reactions cannot be completely avoided. However, referred to the previously mentioned known process, this already results in a quite considerable reduction of the amount of reducing agent needed.

By means of this manner of carrying out the reaction, under normal conditions there is obtained a relatively pure azosemide, which is free from greasy impurities and from impurities which are difficult to separate off and which can be obtained pure by simple recrystallisation.

The following Examples are given for the purpose of illustrating the present invention:

EXAMPLE 1

75 g. 5-(4'-Chloro-5'-sulfamoyl-2'aminophenyl)-tetrazole (amine III) are dissolved at 50° to 60° C. in 450 ml. dimethyl sulphoxide and cooled to ambient temperature. After adding 22.5 g. polyphosphoric acid and 44 ml. thiophene-2-aldehyde, the reaction mixture is stirred for 3 hours at ambient temperature.

Thereafter, 90 ml. dimethyl sulphoxide are distilled off under vacuum (2 to 5 mm.Hg) over the course of 1 hour. A further 10 ml. thiophene-2-aldehyde are now added thereto and the reaction mixture stirred for another 15 minutes at 40°-55° C.

After cooling, the solution is added dropwise in the course of about 15 minutes to a previously prepared solution of 30 g. potassium boranate in 600 ml. dimethyl sulphoxide, the internal temperature thereby being kept between 35° to 40° C. The reaction mixture is subsequently stirred for 3 hours at 35° to 40° C. and 50 ml. methanol then added thereto.

A solution of 200 g. sodium chloride in 1.5 liters 1 N hydrochloric acid is then allowed to run in, with cooling, in the course of about 30 minutes at about 30° C. The reaction mixture is then stirred overnight at ambient temperature and filtered with suction and the substance washed with water until it no longer has mineral acidity and dried in a vacuum at 60° C.

The yield is 100.5 g. and the degree of purity, according to high pressure liquid chromatography, is 95.5%.

After dissolving in a fivefold amount (592 ml.) of dimethylformamide at 75° C. and charcoaling with 5% (6 g.) active charcoal, 5 parts (592 ml.) of water are added thereto at 60° C. and finally 0.33 parts (39 ml.) 2 N hydrochloric acid added thereto. The reaction mixture is cooled to 0° to 5° C., suction filtered the next morning, then washed with ice water and dried in a vacuum at 60° C.

The yield is 88 g. and the degree of purity, according to high pressure liquid chromatography, is 99.5%.

EXAMPLE 2

75 g. Amine III are dissolved in 450 ml. dimethyl sulphoxide at 50° C. and, after the addition of 11.2 g. polyphosphoric acid and 45 ml. thiophene-2-aldehyde, stirred for 1 hour at 50° to 55° C. Thereafter, about 75 ml. dimethyl sulphoxide are continuously distilled off over the course of 1 hour at an internal temperature of 50° to 60° C. After the addition of a further 11 ml. thiophene-2-aldehyde, about 75 ml. dimethyl sulphoxide are again distilled off over the course of another hour. The reaction mixture is cooled to ambient temperature and a solution of 15 g. potassium boranate in 480 ml. dimethyl sulphoxide allowed to run in in the manner described in Example 1. After a subsequent reaction period of 2 hours at 35° to 40° C., hydrolysis is carried out by the dropwise addition of a solution of 165 g. sodium chloride in 1250 ml. 1.2 N hydrochloric acid. The reaction mixture is further worked up in the manner described in Example 1. The yield is 100.6 g. and the degree of purity is 95.1%.

EXAMPLE 3

75 g. Amine III are dissolved in 300 ml. dimethyl sulphoxide and 150 ml. toluene and, after the addition of 15 g. polyphosphoric acid and 45 ml. thiophene-2-aldehyde, stirred for 30 minutes at ambient temperature. 75 ml. Toluene are then distilled off in a vacuum (20 to 30 mm.Hg) at an internal temperature of 45° to 60° C. After 1 hour, a further 11 ml. thiophene-2-aldehyde are added thereto and another 75 ml. toluene distilled off in a vacuum in the course of 1 hour. Thereafter, about 30 ml. of a dimethyl sulphoxide-toluene mixture are distilled off at 15 mm.Hg. The subsequent reduction and working up are carried out in a manner analogous to that used in Example 2. The yield is 97 g. and the degree of purity is 93.85%.

EXAMPLE 4

75 g. Crude amine III are dissolved in 450 ml. dimethyl sulphoxide and, after the addition of 9 g. concentrated sulphuric acid and 45 ml. thiophene-2-aldehyde, the reaction mixture is stirred for 1 hour at 50° to 55° C. The further working up is carried out in the manner described in Example 2. The yield is 95 g. and the degree of purity, according to high pressure liquid chromatography, is 88.9%.

EXAMPLE 5

75 g. Crude amine III are dissolved in 450 ml. dimethyl sulphoxide and, after the addition of 7.5 g. polyphosphoric acid and 45 ml. thiophene-2-aldehyde, the reaction mixture is stirred for 30 minutes at 50° to 60° C. The reaction mixture is then heated to 100° C. and 75 ml. dimethyl sulphoxide are distilled off over the course of about 30 minutes. A further 11 ml. thiophene-2-aldehyde are now added, whereupon a further 75 ml. dimethyl sulphoxide are distilled off at 100° C. The reaction mixture is then cooled to 30° C. and further worked up in the manner described in Example 2. The yield is 100 g. and the degree of purity, according to high pressure liquid chromatography, is 77.9%.

EXAMPLE 6

The Schiff base is prepared in a manner analogous to that described in Example 1. 20 g. Potassium boranate are introduced into the reaction solution at an internal temperature of 40° C. within the course of 30 minutes. Subsequently, the reaction mixture is stirred for 1 hour at 35° to 40° C.

After the addition of 90 ml. methanol the solution is allowed to run into 200 ml. 4 N hydrochloric acid. The further working up is carried out in the manner described in Example 1. The yield is 95 g. and the degree of purity, according to high pressure liquid chromatography, is 97.5%.

EXAMPLE 7

The Schiff base is prepared in a manner analogous to that described in Example 4 except that, instead of 9 g. concentrated sulphuric acid, 2.5 g. anhydrous zinc chloride are used.

Reduction with 14 g. potassium boranate in 480 ml. dimethyl sulphoxide is carried out at 40° to 45° C. and the subsequent reaction time is 1 hour at 40°-45° C.

Further working up is carried out in the manner described in Example 2.

It will be understood that the specification and examples are illustrative but not limitative of the present invention and that other embodiments within the spirit and scope of the invention will suggest themselves to those skilled in the art.

What is claimed is:

1. In a process for the preparation of 5-(4'-chloro-5'-sulfamoyl-2'-thenylamino)-phenyltetrazole by condensing 5-(4'chloro-5'-sulfamoyl-2'-aminophenyl)-tetrazole with thiophene-2-aldehyde in the presence of an acid catalyst, azeotropically distilling off the water formed, reducing the 5-[4'-chloro-5'-sulfamoyl-2'-(thenylidene-2-amino)-phenyl]-tetrazole so obtained with a boranate, and carrying out the reduction in the same medium without prior isolation of the 5-[4'-chloro-5'-sulfamoyl-2'-(thenylidene-2-amino)-phenyl]-tetrazole, the improvement comprising carrying out the condensation in dimethyl sulfoxide as a solvent.

2. Improvement as claimed in claim 1, wherein, per mole of 5-(4'-chloro-5'-sulfamoyl-2'-aminophenyl)-tetrazole, there is used 1.1 to 3 mole thiophene-2-aldehyde.

3. Improvement as claimed in claim 2, wherein, per mole of 5-(4'-chloro-5'-sulfamoyl-2'-aminophenyl)-tetrazole, there is used 1.5 to 2 mole thiophene-2-aldehyde.

4. Improvement as claimed in claim 1, wherein the reduction is carried out with the use of 2 to 10 mole equivalents of boranate.

5. Improvement as claimed in claim 4, wherein the reduction is carried out with the use of 2 to 4 mole equivalents of boranate.

6. Improvement as claimed in claim 1, wherein 0.05 to 0.5 mole of acid catalyst is used.

7. Improvement as claimed in claim 1, wherein the mineral acid or a Lewis acid is used as the acid catalyst.

8. Improvement as claimed in claim 7, wherein the acid catalyst is phosphoric acid, polyphosphoric acid, sulphuric acid, hydrochloric acid, zinc chloride or aluminium chloride.

9. Improvement as claimed in claim 1, wherein the reaction is carried out at a temperature of 20° to 100° C.

10. Improvement as claimed in claim 9, wherein the reaction is carried out at a temperature of 45° to 70° C.

* * * * *